(12) United States Patent
Tung

(10) Patent No.: US 11,524,084 B2
(45) Date of Patent: Dec. 13, 2022

(54) ULTRAVIOLET FACE SHIELD SYSTEMS FOR REDUCING GERM TRANSMISSION

(71) Applicant: Matthew Jay Tung, San Diego, CA (US)

(72) Inventor: Matthew Jay Tung, San Diego, CA (US)

( * ) Notice: Subject to any disclaimer, the term of this patent is extended or adjusted under 35 U.S.C. 154(b) by 342 days.

(21) Appl. No.: 16/826,274

(22) Filed: Mar. 22, 2020

(65) Prior Publication Data

US 2021/0290793 A1  Sep. 23, 2021

(51) Int. Cl.
*A61L 2/10* (2006.01)
*A61L 2/26* (2006.01)
*A41D 13/11* (2006.01)

(52) U.S. Cl.
CPC ............ *A61L 2/10* (2013.01); *A41D 13/1184* (2013.01); *A61L 2/26* (2013.01); *A61L 2202/11* (2013.01)

(58) Field of Classification Search
None
See application file for complete search history.

(56) References Cited

U.S. PATENT DOCUMENTS

| | | |
|---|---|---|
| 4,701,965 A | 10/1987 | Landis et al. |
| 4,856,508 A | 8/1989 | Tayebi et al. |
| 4,965,887 A | 10/1990 | Paoluccio et al. |
| 5,054,480 A * | 10/1991 | Bare .............. A41D 13/11 128/206.28 |
| 5,165,395 A | 11/1992 | Ricci et al. |
| 5,181,506 A | 1/1993 | Tardiff et al. |
| 5,544,361 A | 8/1996 | Fine et al. |
| 6,176,239 B1 | 1/2001 | Grove et al. |
| 6,381,750 B1 | 5/2002 | Mangan et al. |
| 6,470,888 B1 | 10/2002 | Matter et al. |
| 6,523,179 B1 | 2/2003 | Zegarelli et al. |
| 6,543,450 B1 | 4/2003 | Flynn et al. |
| 6,681,765 B2 | 1/2004 | Wen et al. |
| 6,763,835 B1 | 7/2004 | Grove et al. |
| 7,036,502 B2 | 5/2006 | Manne et al. |
| 7,152,600 B2 | 12/2006 | Freriks et al. |
| 7,506,992 B2 | 3/2009 | Carter et al. |
| 7,523,750 B2 | 4/2009 | Krzsztofik et al. |
| 7,845,351 B2 | 12/2010 | Mathis et al. |
| 8,074,648 B2 | 12/2011 | Betz et al. |
| 8,397,715 B2 | 3/2013 | Litz et al. |
| 8,640,265 B2 | 2/2014 | Duncan et al. |
| 8,733,356 B1 | 5/2014 | Roth et al. |
| 8,960,190 B2 | 2/2015 | James et al. |
| 9,827,723 B2 | 11/2017 | Klockseth et al. |

(Continued)

FOREIGN PATENT DOCUMENTS

WO  WO2002065972  8/2002

OTHER PUBLICATIONS

Welch et al., "Far-UVC light: A new tool to control the spread of airborne-mediated microbial diseases," Scientific Reports (2018) vol. 8, Article No. 2752 pp. 1-7.

*Primary Examiner* — Andrew Smyth
(74) *Attorney, Agent, or Firm* — Elizabeth A. G. Cisar

(57) ABSTRACT

Several embodiments relating to ultraviolet face shield systems and methods of use are provided herein. Such face shield systems feature an ultraviolet light source capable of inactivating, destroying, or killing germs, bacteria, viruses, or other pathogens such as human coronavirus COVID-19, and protecting individual(s) from infection.

19 Claims, 12 Drawing Sheets

(56) References Cited

U.S. PATENT DOCUMENTS

| | | | |
|---|---|---|---|
| 10,207,129 | B2 | 2/2019 | Koehler et al. |
| 10,335,618 | B2 | 7/2019 | Zhou et al. |
| 10,426,852 | B2 | 10/2019 | Dobrinsky et al. |
| 10,525,292 | B2 | 1/2020 | Tang et al. |
| 2003/0205137 | A1 | 11/2003 | Bolduc et al. |
| 2005/0241642 | A1 | 11/2005 | Krzysztofik et al. |
| 2006/0130846 | A1 | 6/2006 | Rife et al. |
| 2006/0254592 | A1 | 11/2006 | Anders et al. |
| 2007/0101867 | A1 | 5/2007 | Hunter et al. |
| 2007/0289592 | A1 | 12/2007 | Sutton et al. |
| 2009/0004047 | A1 | 1/2009 | Hunter et al. |
| 2009/0205664 | A1 | 8/2009 | Lyon et al. |
| 2010/0257659 | A1 | 10/2010 | Hitch et al. |
| 2012/0279503 | A1 | 11/2012 | Zhou et al. |
| 2015/0151147 | A1 | 6/2015 | Fun et al. |
| 2015/0375019 | A1 | 12/2015 | VanDerWoude et al. |
| 2017/0157435 | A1 | 6/2017 | Choi et al. |
| 2017/0348445 | A1 * | 12/2017 | Bogdanovich .......... F21V 5/007 |
| 2018/0236275 | A1 | 8/2018 | Song et al. |
| 2019/0015541 | A1 | 1/2019 | Peczalski et al. |
| 2019/0038863 | A1 | 2/2019 | Chang et al. |
| 2019/0125011 | A1 | 5/2019 | Eisenbrey et al. |
| 2019/0174860 | A1 | 6/2019 | VanDerWoude et al. |
| 2019/0175021 | A1 | 6/2019 | Steinbach et al. |
| 2019/0232012 | A1 | 8/2019 | Pedro et al. |
| 2019/0255370 | A1 | 8/2019 | Seppala et al. |

\* cited by examiner

ULTRAVIOLET FACE SHIELD SYSTEMS FOR REDUCING GERM TRANSMISSION

BACKGROUND

Human viruses periodically cause large scale epidemics or pandemics infecting and killing thousands of people. The current 2019-2020 coronavirus pandemic, called COVID-19, is caused by the human coronavirus SARS-CoV-2. Mainstream media often refers to the virus itself and the disease it causes interchangeably as COVID-19. More than 330,000 infected people and 14,000 deaths in over 191 countries have been reported as of Mar. 22, 2020 and the numbers grow every day.

Unlike previous human coronaviruses SARS and MERS, which did not reach pandemic status, COVID-19 has become a global pandemic with widespread transmission because of its high contagiousness, long incubation period of 2-14 days, and lower mortality rate. Some infected individuals exhibit no symptoms at all or only mild symptoms like the common cold; these "super spreaders" are capable of transmitting the virus unknowingly. Outside of China where COVID-19 first broke out and has killed over 3,000 people before stabilizing, the numbers are getting worse by the day. The World Health Organization (WHO) reported that the death rate is doubling every 11 days in the world on average as of Mar. 16, 2020.

Italy has been the hardest hit outside of China and the numbers are not improving. Italy reported 59,138 total cases and 5,476 deaths as of Mar. 22, 2020, with 5,560 new cases and 651 new deaths reported on that day. The death rate is doubling every 4 days according to the WHO. The country has been on mandatory lockdown and does not have the healthcare capacity to treat all the COVID-19 positive people. Many other European countries are reporting over a thousand new cases a day including Spain (3,107), Germany (2,488), and France (1,559).

COVID-19 has been disastrous in the United States from a public health and economic standpoint. As of Mar. 22, 2020, 32,356 total cases of COVID-19 and 414 deaths have been reported. The United States reported 8,149 new daily cases on Mar. 22, 2020. COVID-19 has also tanked the economy. The Dow Jones Industrial Average dropped 2,353 points on Mar. 12, 2020, which was the worst single day drop in history until the Dow dropped 2,997 points on Mar. 16, 2020 over fears of a global recession. The Dow has plummeted from approximately 30,000 to 20,000 points over the past month. Massive layoffs have surged. 18% of US workers have lost their jobs or had hours cut. Moody's Analytics reported that half of all US jobs are at risk and 18%. The US Treasury Secretary has warned senators that unemployment could hit 20% unless the federal government intervenes with an economic stimulus package in the trillion dollar range.

Several US states have shut down public schools, bars, and restaurants indefinitely. Many cities, such as those in the California Bay Area, have ordered residents to shelter-in-place. Public gatherings of more than 10 people are not allowed.

Compounding the problem in the US is the lack of available testing and unpreparedness. Many states have not been able to test symptomatic individuals. In fact, the US lags far behind other countries in the number of available tests per capita. Whereas South Korea has performed 316,664 tests and has 6,148 tests per million people as of Mar. 16, 2020, the US has only performed 103,945 tests as of Mar. 19, 2020 and only has 125 tests per million people as of Mar. 17, 2020. Even Italy, the hardest hit country outside of China, has performed tests and has 1,005 tests per million people as of Mar. 16, 2020.

The US also trails other countries in overall healthcare infrastructure to handle the pandemic. South Korea has 12.3 hospital beds per 1,000 people, while the US has 2.8. Even Italy has 3.2 hospital beds per 1,000. The fact that the numbers are getting worse in Italy despite having more tests and hospital beds per capita than the US does not bode well for the US.

There is an urgent need to reduce or prevent transmission of COVID-19 worldwide. No FDA approved therapies or vaccines are available. It is estimated that a vaccine may not be available for over a year and there are reports that a vaccine may not be totally effective in view of viral mutation. Already, two strains of COVID-19 have been reported, a more aggressive L-type and S-type, and both are involved in the pandemic. Clinical trials are ongoing for the antiviral drug remdesivir, which has been given to some patients under compassionate use with anecdotal positive results. However, even if remdesivir is approved for COVID-19 treatment, it is administered in a hospital to severe COVID-19 patients who need hospitalization and cannot shelter in place or quarantine at home for the duration of infection. While remdesivir in theory could dampen the mortality rate assuming the health care system finds a way to accommodate every severely sick COVID-19 patient, it seems unlikely remdesivir would help prevent widespread transmission from asymptomatic or mildly symptomatic super spreaders. The CDC has projected between 160-214 million people in the US could be infected over the course of the epidemic and as many as 200,000 to 1.7 million people could die. There is a pressing need to "flatten the coronavirus curve."

SUMMARY

Face shields, face masks, and face systems provided herein are capable of preventing or reducing transmission of germs, bacteria, viruses, or other pathogens such as COVID-19, and protecting individual(s) from infection. Such embodiments described herein overcome deficiencies of existing means of protecting individuals from infection.

The CDC does not recommend the routine use of respirators within the community. According to the CDC, a respirator is a personal protective device that is worn on the face or head and covers at least the nose and mouth. Common examples of respirators include the N95 filtering facepiece respirator (FFR) that removes particles from the inhaled air. The most widely used type of respirator by the general public is a simple face mask that covers the nose and mouth, but not the eyes, and has straps that fit around the ears.

Existing face masks are not sufficient to reduce transmission of infection such as COVID-19. One problem with existing face masks is that they don't cover the eyes. COVID-19 is known to infect through the eyes, whether directly from an infected individual sneezing or coughing or when people have COVID-19 on their hands and rub their eyes. Another problem is the shortage of these masks. Indeed, the CDC recommends the general public not wear these masks because they are not effective in preventing spread of COVID-19 anyway and the supply should be reserved for symptomatic individuals and health care professionals who are running out of them. Furthermore, the US Surgeon General commented that many masks are not worn properly and do not form a snug seal around the face. Yet another problem with face masks is their disposability. Each mask is suitable only for single use and must be discarded, otherwise COVID-19 viruses on the mask can cause infection if the mask is reused or not properly discarded. Single use disposability of these masks also contributes to their low supply. As a consequence of face mask shortages in the US, it has been reported on Mar. 19, 2020 that health care providers will have to resort to wearing scarves or bandanas instead of face masks, and continue to provide care even if they themselves are positive for the COVID-19 virus.

Respirators that cover the eyes, nose, and mouth also suffer from the problem of complicated post-use sterilization that makes them impractical for community use. An example of this type of respirator is the powered air-purifying respirator (PAPR), which covers the entire face and uses HEPA filters to block viral exposure. However, they need to be cleaned and disinfected, and the filters must be discarded and replaced. Existing respirators themselves are "fomites," infectious contaminated surfaces like door handles. According to the National Institutes of Health, the COVID-19 virus can be detected up to 4 hours on copper, up to 24 hours on cardboard and up to 2-3 days on plastic and stainless steel. Existing respirators are intended to serve as physical barriers against viruses, but do not inactivate them; consequently, these existing respirators themselves become fomites capable of transmitting the virus.

BRIEF DESCRIPTION OF THE DRAWINGS

The figures illustrate several embodiments and are not limiting on other embodiments described herein.

DETAILED DESCRIPTION

Figure 1:
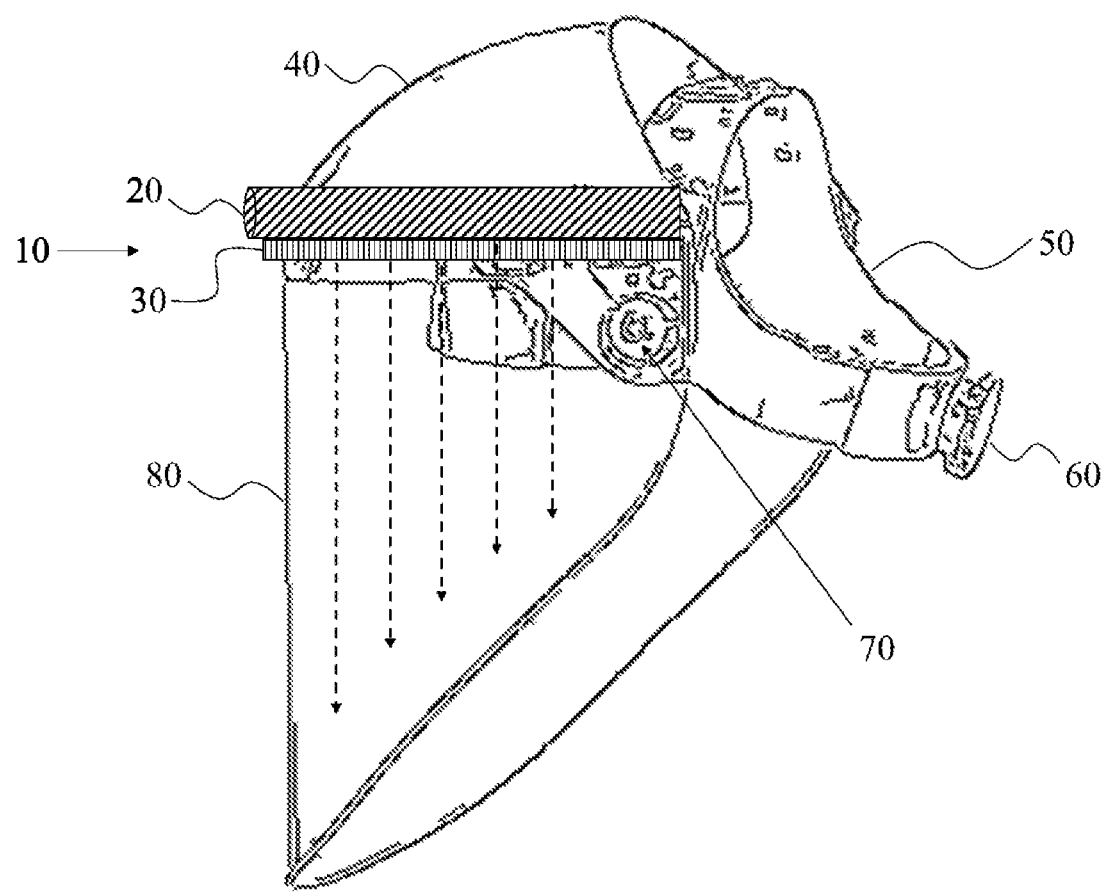
FIG. 1 is a perspective view of an ultraviolet face shield system including a ratchet headgear style head mount, face shield, and ultraviolet light source.

As used herein, "COVID-19 virus" refers to the human coronavirus SARS-CoV-2 and as used herein, "COVID-19" refers to coronavirus disease 2019 associated with SARS-CoV-2 infection.

As used herein, "SARS-CoV-2" refers to all strains and gene sequences of the human coronavirus associated with the COVID-19 pandemic. SARS-CoV-2 is the name given by the International Committee on Taxonomy of Viruses. Several genome sequences of SARS-CoV-2 have been submitted to Genbank including but not limited to Accession Numbers MN908947, MN985325.1 (Holshue et al., 2020), LC528232, and LR757996.

As used herein, "inactivate," "kill," or "destroy," in the context of the COVID-19 virus or SARS-CoV-2 means to reduce the infectivity of the virus. Reducing the infectivity of the virus can mean reducing the infectious titer or half life of the virus.

As used herein, the "top" of a face shield refers to the end of the face shield that aligns with the top of a user's face near the user's forehead or top of the head.

As used herein, the "bottom" of a face shield refers to the end of the face shield that aligns with the bottom of a user's face near or below the user's chin.

As used herein, an "ultraviolet light source" can, but does not necessarily, include a single ultraviolet lamp or single ultraviolet LCD. In several embodiments, an ultraviolet light source can include a plurality of ultraviolet lamps or ultraviolet LCDs. In certain embodiments, an ultraviolet light source comprises a housing containing one or more ultraviolet lamps or ultraviolet LCDs and has a single power source for the one or more ultraviolet lamps or ultraviolet LCDs. In certain embodiments, distinct ultraviolet light sources have their own power sources.

Several embodiments are directed to an ultraviolet face shield system comprising at least one ultraviolet light source; a face shield comprising an inner surface configured for facing the face of a user and an outer surface; and a head mount, wherein at least one ultraviolet light source is positioned to emit ultraviolet light in front of, around, on, or over the outer surface of the face shield and wherein the ultraviolet light is capable of inactivating, destroying, or killing viruses, such as the COVID-19 virus.

Unlike existing face masks and respirators, such embodiments can simultaneously protect the user from viral exposure or infection and inactivate the virus in real time. Unlike existing face masks and respirators, such embodiments are self-sanitizing or disinfecting and do not need to be discarded after single use. Furthermore, unlike existing face masks and respirators, such embodiments themselves do not become fomites capable of infecting the user or others. Such embodiments help solve the current respirator and face mask shortage besetting the healthcare industry and public at large. Also, unlike existing face masks and respirators, such embodiments protect the user's full face; the face shield covers the eyes, nose, and mouth while the ultraviolet light kills the virus in an area in front of, around, on, or over the face shield.

Certain embodiments of ultraviolet face shield systems described herein feature a plurality of ultraviolet light sources. Having a plurality of ultraviolet light sources can expand the zone or area around the face shield system for inactivating viruses and protecting the user. Ultraviolet light sources can operate together and provide a kill zone against the virus. In certain embodiments, an ultraviolet light source is attached to the head mount and positioned to emit ultraviolet light in front of, around, on, or over the outer surface of the face shield. In certain embodiments, an ultraviolet light source is attached to the face shield and positioned to emit ultraviolet light in front of, around, on, or over the outer surface of the face shield. In certain embodiments, an ultraviolet light source is attached to the outer surface of the face shield and positioned to emit ultraviolet light in front of, around, on, or over the outer surface of the face shield. In certain embodiments, the face shield and the ultraviolet light source are attached to the head mount, wherein the ultraviolet light source is positioned to emit ultraviolet light in front of, around, on, or over the outer surface of the face shield. In certain embodiments, the ultraviolet light source protrudes over the outer surface of the face shield. In certain embodiments, the ultraviolet light source is attached to the face shield and protrudes over the outer surface of the face shield. In certain embodiments, the ultraviolet light source is attached to the head mount and protrudes over the outer surface of the face shield.

In certain embodiments, the ultraviolet light source can be adjusted to face and emit ultraviolet light in any desired direction. In certain embodiments, the ultraviolet light source can comprise a housing capable of swiveling, rotating, or oscillating, thereby allowing the user to adjust the angle of the ultraviolet light in any desired direction. In certain embodiments, the ultraviolet light source can oscillate up and down or side to side, thereby sweeping an area around the ultraviolet face shield system. In any of the foregoing embodiments, the ultraviolet light can be capable of inactivating, destroying, or killing germs, bacteria, viruses, or other pathogens, including but not limited to the COVID-19 virus.

In certain embodiments, an ultraviolet face shield system comprises a plurality of ultraviolet light sources, wherein at least one ultraviolet light source is positioned to emit ultraviolet light in front of, around, on, or over the outer surface of the face shield and at least one ultraviolet light source is positioned to emit ultraviolet light away from the face shield. In certain embodiments, both light sources are attached to the head mount. In certain embodiments, a plurality of ultraviolet light sources are attached to the face mask. In certain embodiments, an ultraviolet light source positioned to emit ultraviolet light in front of, around, on, or over the outer surface of the face shield is attached to the head mount, and an ultraviolet light source positioned to emit ultraviolet light away from the face shield is attached to the face shield. In certain embodiments, an ultraviolet light source positioned to emit ultraviolet light in front of, around, on, or over the outer surface of the face shield is attached to the face shield, and an ultraviolet light source positioned to emit ultraviolet light away from the face shield is attached to the head mount.

Several embodiments are directed to an ultraviolet face shield system comprising at least one ultraviolet light source; a face shield comprising an inner surface configured for facing the face of a user and outer surface; a head mount; and at least one ultraviolet reflector. The ultraviolet reflector is designed to protect the user's body below the face from exposure to the ultraviolet light by reflecting or redirecting it. Furthermore, the ultraviolet reflector is designed to provide a more defined, focused, or concentrated area around the face shield system for killing the virus. The ultraviolet reflector can be positioned in a location or angle to reflect or redirect to the ultraviolet light toward any desired direction. In certain embodiments, the ultraviolet reflector and ultraviolet light source face each other, wherein the ultraviolet reflector is positioned under the face shield and is configured to reflect ultraviolet light emitted from an ultraviolet light source positioned above the face shield. In certain embodiments, the reflected ultraviolet light can be redirected back up towards the ultraviolet light source or away from the face shield and user.

In any of the foregoing embodiments, the ultraviolet reflector can be curved. In any of the foregoing embodiments, the ultraviolet reflector can comprise an upper surface and a lower surface. In any of the foregoing embodiments, the upper surface of the ultraviolet reflector can face the ultraviolet light source, which is positioned above the ultraviolet reflector. In any of the foregoing embodiments, the upper surface of the curved ultraviolet reflector can be the concave side. In any of the foregoing embodiments, the face shield can be positioned between the ultraviolet reflector and the ultraviolet receptor. In any of the foregoing embodiments, the ultraviolet reflector can protrude from the face shield. In any of the foregoing embodiments, the ultraviolet reflector can be attached to the face shield. In any of the foregoing embodiments, the ultraviolet reflector can be attached to the head mount.

Certain embodiments of ultraviolet face shield systems described herein feature a plurality of ultraviolet reflectors. In certain embodiments, an ultraviolet face shield system comprises an ultraviolet light source located between an upper ultraviolet reflector and a lower ultraviolet reflector. In certain embodiments, the ultraviolet light emitted from the ultraviolet light source will reflect back and forth between the ultraviolet reflectors. In certain embodiments, the upper ultraviolet reflector is attached to the face shield or head mount and protrudes over an ultraviolet light source located below the ultraviolet reflector. In certain embodiments, the lower ultraviolet reflector is attached to the face shield or head mount and protrudes over the user's torso when worn by the user.

In any of the foregoing embodiments, the ultraviolet light source can be positioned to emit ultraviolet light in front of, around, on, or over the outer surface of the face shield and the ultraviolet reflector. In certain embodiments, the ultraviolet reflector is configured to reflect ultraviolet back toward the ultraviolet light source. In certain embodiments, the ultraviolet reflector is configured to reflect ultraviolet light outward and away from the face shield.

Face Shields

In any of the foregoing embodiments, the face shield can be made of transparent or substantially transparent plastic. As used herein, "transparent" means suitable for a user to see through. In certain embodiments, the face shield is optically clear. In certain embodiments, the face shield can be a single piece of curved plastic wherein the inner surface of the face shield is the concave side of the curved plastic and the outer surface of the face shield is the convex side. In certain embodiments, the concave side of the curved plastic face shield is configured for facing the face of the user. In certain embodiments, the plastic is polycarbonate.

In any of the foregoing embodiments, the face shield can be capable of blocking ultraviolet light. In certain embodiments, the face shield is capable of reducing, preventing, or blocking ultraviolet light emitted from the ultraviolet light source from passing through the outer surface of the face shield to the inner surface of the face shield. The user of the ultraviolet face shield system is protected from germs, bacteria, viruses, or other pathogens, including but not limited to the COVID-19 virus, by operation of the ultraviolet light inactivating, destroying, or killing them in the area around the outer surface of the face shield. Meanwhile, the ultraviolet resistant or blocking face shield protects the user from the ultraviolet light.

In any of the foregoing embodiments, the plastic face shield can be made of polycarbonate, proprionate, polyethylene, or acrylic plastic. In any of the foregoing embodiments, the face shield can contain ultraviolet absorbing and/or reflecting additives. In any of the foregoing embodiments, the face shield is capable of blocking, reflecting, or absorbing ultraviolet light having wavelengths from about 100-400 nm, about 100-280 nm (UVC), about 280-315 nm (UVB), or about 315-400 nm (UVA). In certain embodiments, the face shield is capable of blocking or reflecting broad spectrum UVC ultraviolet light having wavelengths between 200-400 nm, which destroys viruses but can damage skin. In certain embodiments, the face shield is capable of blocking or reflecting far-UVC spectrum ultraviolet light having wavelengths between 207-222 nm, which destroys viruses without damaging skin. As used in the context of ultraviolet light wavelengths, "about" means+/−10% of any specified value.

In certain embodiments, the face shield is capable of blocking, reflecting, or absorbing at least about 85%, at least about 90%, at least about 95%, at least about 99%, or 100% of ultraviolet light having wavelengths from about 200-400 nm.

In certain embodiments, the face shield is capable of blocking, reflecting, or absorbing at least about 85%, at least about 90%, at least about 95%, at least about 99%, or 100% of ultraviolet light having wavelengths from about 207-222 nm.

In certain embodiments, the face sheet meets the ANSI Z87.1 standard.

In any of the foregoing embodiments, the face shield can have a thickness in the range of about 0.1 mm to about 3.0 mm. In any of the foregoing embodiments, the face shield can be about any of the following thicknesses: 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, or 3.0 mm. As used in the context of face shield thickness, "about" means+/−10% of any specified value.

In any of the foregoing embodiments, the face shield, as oriented from the perspective of a user wearing an ultraviolet face shield system described herein, can be about any of the following lengths (vertical orientation top to bottom of the face): 6 inches, 7 inches, 8 inches, 9 inches, 10 inches, 11 inches, 12 inches, 13 inches, 14 inches, or 15 inches. In any of the foregoing embodiments, the face shield, as oriented from the perspective of an individual wearing an ultraviolet face shield system described herein, can be about any of the following ranges of lengths (vertical orientation top to bottom of the face): 6-15 inches, 7-15 inches, 8-15 inches, 9-15 inches, 10-15 inches, or any range within. As used in the context of face shield length, "about" means+/−10% of any specified value.

In any of the foregoing embodiments, the face shield, as oriented from the perspective of an individual wearing an ultraviolet face shield system described herein, can be about any of the following widths (horizontal orientation ear to ear): 6 inches, 7 inches, 8 inches, 9 inches, 10 inches, 11 inches, 12 inches, 13 inches, 14 inches, or 15 inches. In any of the foregoing embodiments, the face shield, as oriented from the perspective of an individual wearing an ultraviolet face shield system described herein, can be about any of the following ranges of widths (horizontal orientation ear to ear): 6-15 inches, 7-15 inches, 8-15 inches, 9-15 inches, 10-15 inches, or any range within. As used in the context of face shield width, "about" means+/−10% of any specified value.

In certain embodiments the face shield has a length and width designed to cover a user's entire face.

In certain embodiments, the face shield is attached to the head mount. Any means of attachment is suitable including, but not limited to, universal swivel pattern buttons and notches for detachability, universal hole patterns, screws, glue, epoxy, polymer, velcro, and the like. In certain embodiments, the face shield is materially contiguous with the head mount. In certain embodiments, the face shield and head mount are attached or fused by injection molding. In certain embodiments, the face shield and head mount are both plastic and attached or fused to each other by injection molding. In certain embodiments, the face shield and head mount are fabricated from the same plastic, but are considered attached or fused.

Ultraviolet Light Source

In any of the foregoing embodiments, the ultraviolet light source can comprise an ultraviolet lamp or LED and a housing. In certain embodiments, the housing contains one or more ultraviolet lamps or LEDs. In certain embodiments, the housing is configured to contain one or more ultraviolet lamps or LEDs and direct the ultraviolet light emitted from the ultraviolet lamps or LEDs in a downward direction. In certain embodiments, the housing is configured to direct the ultraviolet light over the outer surface of the face shield. In certain embodiments, the housing is configured to direct the ultraviolet light over an area around the outer surface of the face shield. In certain embodiments, the housing is attached to the face shield. In certain embodiments, the housing is attached to head mount. In certain embodiments, the housing can be attached to both the face shield and the head mount where there are a plurality of ultraviolet light sources on the ultraviolet face shield system.

In any of the foregoing embodiments, the ultraviolet light source is capable of emitting ultraviolet light having wavelengths from about 100-400 nm, about 100-280 nm (UVC), about 280-315 nm (UVB), or about 315-400 nm (UVA). In certain embodiments, the ultraviolet light source is capable of emitting broad spectrum UVC ultraviolet light having wavelengths between 200-400 nm. In certain embodiments, the ultraviolet light source is capable of emitting far-UVC spectrum ultraviolet light having wavelengths between 207-222 nm, which destroys viruses without damaging skin. As used in the context of ultraviolet light wavelengths, "about" means+/−10% of any specified value. It has been reported that broad spectrum UVC and far-UVC spectrum ultraviolet light can destroy viruses. Welch et al., *Scientific Reports* Volume 8, Article number: 2752 (2018), which is incorporated by reference in its entirety.

In any of the foregoing embodiments, the ultraviolet light source is capable of emitting ultraviolet light at an intensity from about 75 to 350 $W/m^2$, 75 to 100 $W/m^2$, 100 to 125 $W/m^2$, 125 to 150 $W/m^2$, 150 to 175 $W/m^2$, 175 to 200 $W/m^2$, 200 to 225 $W/m^2$, 225 to 250 $W/m^2$, 250 to 275 $W/m^2$, 275 to 300 $J/m^2$, 300 to 325 $W/m^2$, and/or 325 to 350 $W/m^2$. In any of the foregoing embodiments, the ultraviolet light source is capable of emitting ultraviolet light at an intensity of from about 100-350 $W/m^2$, 150-525 $W/m^2$ and 250-875 $W/m^2$, 100-525 $W/m^2$, 150-875 $W/m^2$ or 100-875 $W/m^2$.

In any of the foregoing embodiments, the ultraviolet light source is capable of emitting ultraviolet light at an intensity from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 $mJ/cm^2$. It has been reported that a very low dose of 2 $mJ/cm^2$ of 222 nm far-UVC light can destroy viruses. Welch et al., *Scientific Reports* Volume 8, Article number: 2752 (2018), which is incorporated by reference in its entirety.

In any of the foregoing embodiments, the ultraviolet light source can comprise a fluorescent lamp or a light emitting diode (LED), wherein the ultraviolet light source is capable of emitting any of the aforementioned wavelengths of ultraviolet light and/or any of the aforementioned intensities. In certain embodiments, the LED can be a 70 mW UV-C LED. For example, LG has described a 70 mW UV-C LED for sterilization applications having ultraviolet wavelengths in the range of 200-280 nm.

Certain embodiments are directed to an ultraviolet face shield system comprising a plurality of ultraviolet light sources. In certain embodiments, an ultraviolet face shield system comprises one or more lamps and/or LEDs. In certain embodiments, an ultraviolet face shield system comprises between 1-50 lamps and/or LEDs, or any number of lamps and/or LEDs within that range. In certain embodiments, ultraviolet light source is a plurality of UVC LEDs. In certain embodiments, the ultraviolet light source is a fused silica quartz tube having inert gas. In certain embodiments, the fused silica quartz tube having inert gas has a 15-25 mm diameter.

The ultraviolet light source(s) can be any shape. In certain embodiments, the ultraviolet light source is rectangular, cube, square, or curved.

In certain embodiments, an ultraviolet face shield system or ultraviolet light source comprises a power source capable of powering the ultraviolet light source to emit ultraviolet light. The power source may be an input for direct current (DC), for example from a wall outlet. The power source may be configured for replaceable or rechargeable batteries. In certain embodiments, the power source can comprise a disposable battery, a rechargeable battery, or a USB battery port that can be powered or recharged with a USB interfaced power bank or USB stick battery. In certain embodiments, the power source can comprise an internal gel-based, lead-acid battery that can be charged for field operation from a standard wall outlet.

Ultraviolet Reflector

In certain embodiments, an ultraviolet face shield system comprises one or more ultraviolet reflectors. The ultraviolet reflector(s) can be attached to the face shield or head mount. Ultraviolet reflectors can be made of any material suitable for reflecting ultraviolet light including, but not limited to, metal, aluminum, steel, and silica. Additional non limiting examples of suitable ultraviolet reflectors include, but are not limited to, polished aluminum, unpolished aluminum, dichroic aluminum, mirrors, stacked silicon, polytetrafluoroethylene (PTFE), mylar, teflon, and bora silica. Ultraviolet reflectors can be any suitable shape including but not limited to elliptical, curved, arced, circular, semicircular, or flat. Ultraviolet reflectors can have any suitable form including but not limited to sheet form. In certain embodiments, the ultraviolet reflector is an aluminum sheet. Ultraviolet reflectors can have a selected material, shape, or form configured to have a desired reflection focal point. In certain embodiments, an ultraviolet reflector will have a material, shape, or form, and will be positioned on the ultraviolet face shield system to reflect ultraviolet light back toward the ultraviolet light source, or toward another ultraviolet reflector, or toward an area around, above, or in front of the face shield.

Head Mount

In any of the aforementioned embodiments, the ultraviolet face shield system can comprise a head mount configured to position the face shield in front of a user's face. In certain embodiments, the face shield is attached to the head mount. In certain embodiments, the head mount can be any wearable means for positioning the face shield in front of a user's face. Examples of suitable head mounts include, but are not limited to, headbands, helmets, crown helmets, full face helmets, hoods, hats, hard hats, ratchet headgears, visors, and the like. In certain embodiments, the head mount is adjustable and capable of fitting any head size. In certain embodiments, the head mount wraps around a user's head. In certain embodiments, the head mount comprises a brim that protrudes over a user's face. In certain embodiments, one or more ultraviolet light sources described herein are attached to the brim of the head mount. In certain embodiments, one or more ultraviolet light sources described herein are attached under the brim of the head mount. In certain embodiments, one or more ultraviolet light sources described herein are attached on top of the brim of the head mount.

Certain Germs, Bacteria, Viruses, or Other Pathogens

In any of the foregoing embodiments, the ultraviolet face shield system is capable of inactivating, destroying, or killing germs, bacteria, viruses, or other pathogens such as human coronavirus COVID-19. In certain embodiments, the ultraviolet face shield system is capable of inactivating, destroying, or killing influenza viruses, such as type A, type B, or H1N1 influenza viruses. In certain embodiments, the ultraviolet face shield system is capable of inactivating, destroying, or killing coronavirus, such as COVID-19 virus. In certain embodiments, the ultraviolet face shield system is capable of inactivating, destroying, or killing viruses from the family arenaviridae, bunyaviridae, filoviridae, or flaviviridae. Additional types of viruses that can be killed by ultraviolet face shield systems described herein include, but are not limited to, varicella virus, measles virus, mumps virus, hantavirus, Ebola virus, SARS virus, and MERS virus. Viral epidemics and pandemics often involve novel strains of viruses belonging to a known family of viruses. Often, these novel viral strains are zoonotic viruses that cross from a non-human animal to humans. In certain embodiments, the ultraviolet face shield system is capable of inactivating, destroying, or killing zoonotic viruses.

Certain Additional Features

In any of the foregoing embodiments, additional features and components can fit between the face shield and a user's face. In certain embodiments, an ultraviolet face shield system can further comprise goggles, glasses, surgical masks, N95 masks, or N99 masks, wherein these components can be worn under the face shield, which fits over the components.

Certain Numbered Embodiments

The following are certain non-limiting numbered embodiments:

E1. An ultraviolet face shield system for reducing viral transmission comprising:
   a face shield comprising an inner surface configured for facing the face of a user and an outer surface;
   an adjustable head mount, and
   at least one ultraviolet light source;
   wherein the ultraviolet light source is attached to the face shield or the head mount, positioned near the top of the face shield, and configured to emit ultraviolet light over the outer surface of the face shield; and wherein the ultraviolet light is capable of inactivating a virus.

E2. The ultraviolet face shield system of embodiment 1, wherein the ultraviolet light source comprises an ultraviolet lamp or ultraviolet light emitting diode (LED) capable of emitting broad spectrum ultraviolet C (UVC) light having a wavelength between 200-400 nm or far-UVC spectrum light having a wavelength between 207-222 nm.

E3. The ultraviolet face shield system of embodiment 1 or 2, wherein the face shield is curved, plastic, 8 to 15 inches wide, and 8 to 15 inches long, wherein the concave side of the curved plastic face shield is the inner surface of the face shield and the convex side of the curved plastic face shield is the outer surface of the face shield.

E4. The ultraviolet face shield system of any of embodiments 1-3, wherein the head mount is a helmet, hood, hat, or ratchet headgear, and the face shield is attached to the head mount.

E5. The ultraviolet face shield system of any of embodiments 1-4, wherein the ultraviolet face shield system further comprises a first ultraviolet reflector attached to the face shield or head mount, wherein the first ultraviolet reflector is positioned near the bottom of the face shield and protrudes outward from the face shield, and wherein the first ultraviolet reflector comprises an upper surface and a lower surface wherein the upper surface of the first ultraviolet reflector faces the ultraviolet light source and is configured to reflect ultraviolet light emitted from the ultraviolet light source back towards the ultraviolet light source or away from the face shield.

E6. The ultraviolet face shield system of any of embodiments 1-5, wherein the ultraviolet face shield system comprises a second ultraviolet reflector attached to the face shield or head mount near the top of the face shield and protrudes from the face shield, wherein the ultraviolet light source is positioned between the first ultraviolet reflector and the second ultraviolet reflector, and wherein the second ultraviolet reflector comprises an upper surface and a lower surface wherein the lower surface of the second ultraviolet reflector faces the upper surface of the first ultraviolet reflector.

E7. The ultraviolet face shield system of any of embodiments 1-6, wherein the first ultraviolet reflector comprises metal, aluminum, steel, silica, polytetrafluoroethylene (PTFE), mylar, or teflon.

E8. The ultraviolet face shield system of any of embodiments 1-7, wherein the second ultraviolet reflector comprises metal, aluminum, steel, silica, polytetrafluoroethylene (PTFE), mylar, or teflon.

E9. The ultraviolet face shield system of any of embodiments 1-8, wherein the face shield is polycarbonate, proprionate, polyethylene, or acrylic.

E10. The ultraviolet face shield system of any of embodiments 1-9, wherein the first ultraviolet reflector is elliptical, curved, circular, semicircular, or flat.

E11. The ultraviolet face shield system of any of embodiments 1-10, wherein the second ultraviolet reflector is elliptical, curved, circular, semicircular, or flat.

E12. The ultraviolet face shield system of any of embodiments 1-11, wherein the face shield is polycarbonate and the first and the second ultraviolet reflectors are aluminum.

E13. The ultraviolet face shield system of any of embodiments 1-12, wherein the ultraviolet face shield system comprises a housing containing the ultraviolet light source, wherein the housing is swivelable and configured to adjust the direction the ultraviolet light source faces.

E14. The ultraviolet face shield system of any of embodiments 1-13, wherein the head mount is a ratchet headgear.

E15. The ultraviolet face shield system of any of embodiments 1-14, wherein the head mount is a hat comprising a brim and the ultraviolet light source is attached under the brim.

E16. The ultraviolet face shield system of any of embodiments 1-12, wherein the ultraviolet face shield system further comprises goggles, glasses, a surgical mask, a N95 mask, or a N99 mask, wherein the goggles, glasses, surgical mask, N95 mask, N99 mask are positioned inside the ultraviolet face shield system.

E17. The ultraviolet face shield system of any of embodiments 1-1, wherein the virus is COVID-19 virus.

E18. The ultraviolet face shield system of any of embodiments 1-6, wherein the virus is COVID-19 virus.

E19. A method of reducing viral transmission comprising wearing the ultraviolet face shield system of any of embodiments 1-18 and turning on the ultraviolet light source, thereby killing the virus.

E20. The method of embodiment 19, wherein the virus is COVID-19 virus.

Certain Illustrated Embodiments

Certain non limiting embodiments are illustrated by the Figures.

In FIG. 1, the head mount (4) has an adjustable ratchet headgear (5) that can be configured to fit a user's head by tightening knobs (6) and (7). The face shield (8) is attached to the ratchet headgear (5) by the side tightening knob (7). The ultraviolet light source (1) is located over the face shield (8) and has a housing (2) for the ultraviolet LEDs (3). The ultraviolet light source (1) is positioned to emit ultraviolet light (dashed arrows) downward in front of and over the face shield (8).

Figure 2:
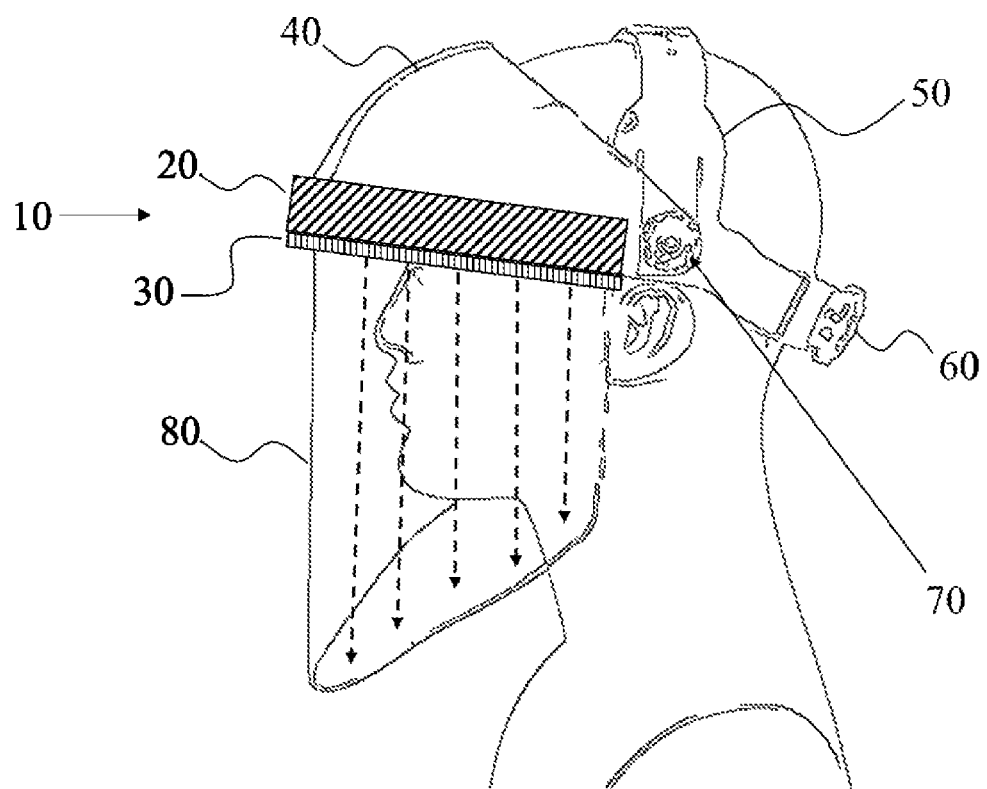
FIG. 2 is a perspective view of an ultraviolet face shield system including a ratchet headgear style head mount, face shield, and ultraviolet light source as worn by a user.

In FIG. 2, a user wears the head mount (40) over the head and adjusts the fit with an adjustable ratchet headgear (50) by tightening knobs (60) and (70). The face shield (80) is attached to the ratchet headgear (50) by the side tightening knob (70) and is positioned in front of the user's face. The ultraviolet light source (10) is located over the face shield (80) and has a housing (20) for the ultraviolet LEDs (30). The ultraviolet light source (10) is positioned to emit ultraviolet light (dashed arrows) downward in front of and over the face shield (80).

Figure 3:
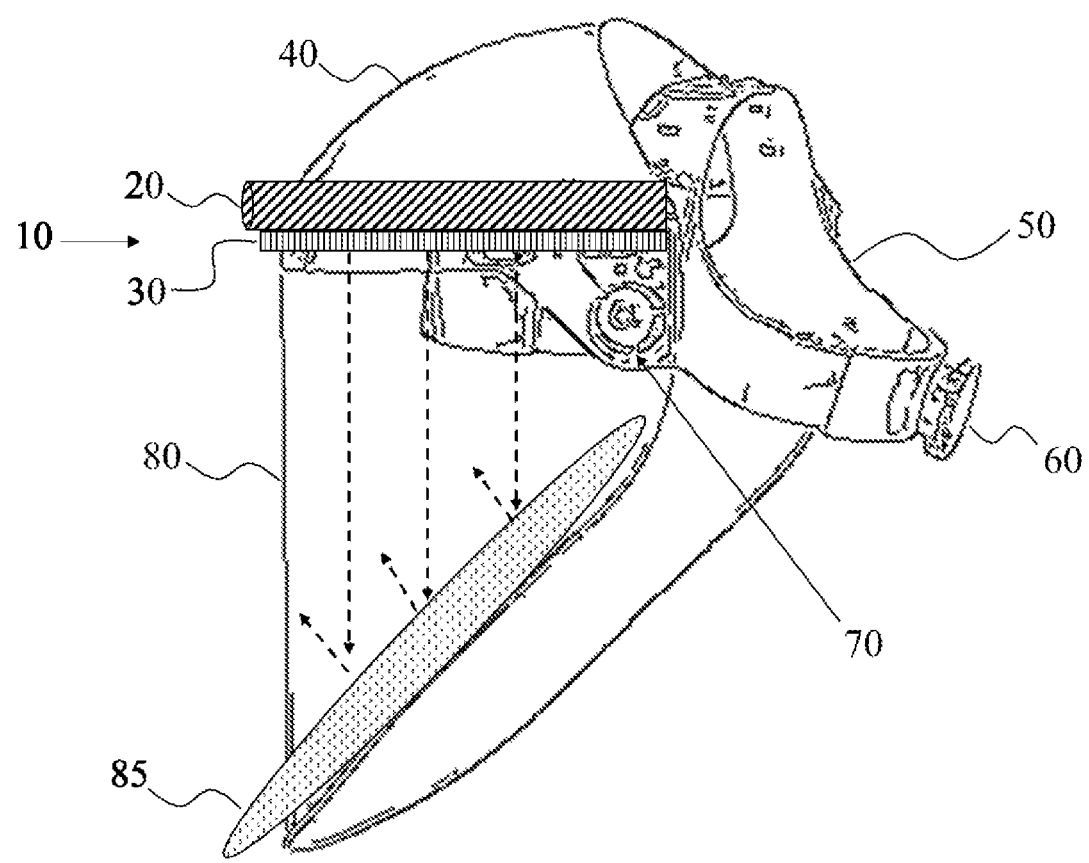
FIG. 3 is a perspective view of an ultraviolet face shield system including a ratchet headgear style head mount, face shield, ultraviolet light source, and ultraviolet reflector.

In FIG. 3, the head mount (40) has an adjustable ratchet headgear (50) that can be configured to fit the user's head by tightening knobs (60) and (70). The face shield (80) is attached to the ratchet headgear (50) by the side tightening knob (70). The ultraviolet light source (10) is located over the face shield (80) and has a housing (20) for the ultraviolet LEDs (30). The ultraviolet light source (10) is positioned to emit ultraviolet light (dashed arrows) downward in front of and over the face shield (80). The ultraviolet reflector (85) is attached to the bottom of the face shield (80) and is configured to reflect ultraviolet light (dashed arrows).

Figure 4:
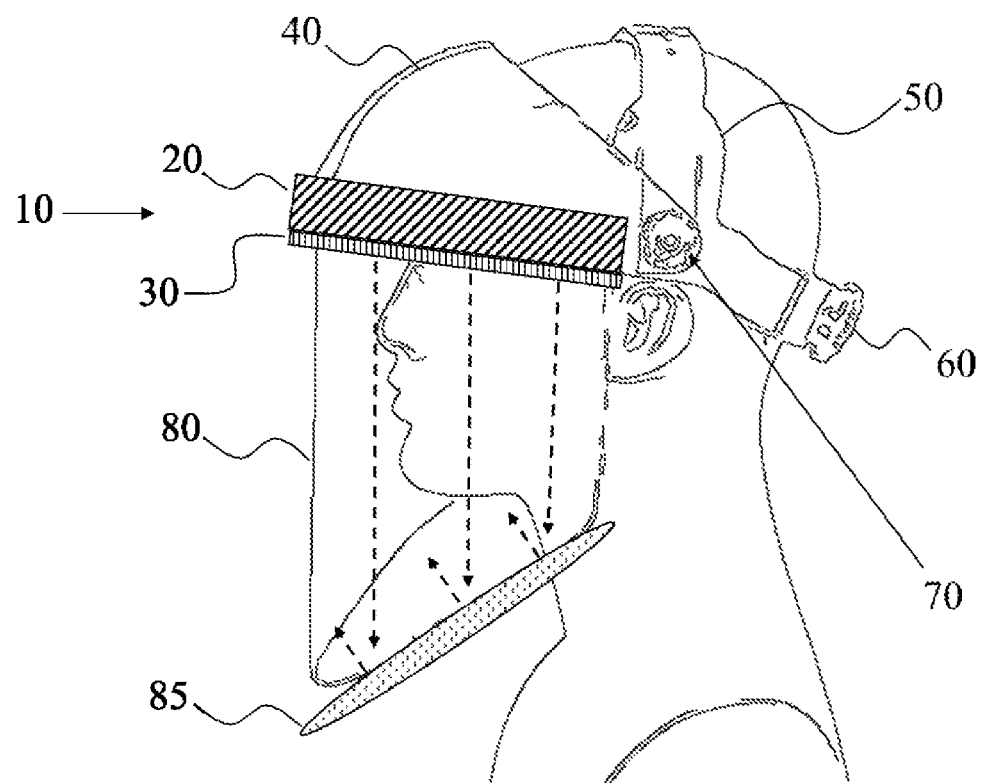
FIG. 4 is a perspective view of an ultraviolet face shield system including a ratchet headgear style head mount, face shield, ultraviolet light source, and ultraviolet reflector as worn by a user.

In FIG. 4, a user wears the head mount (40) over the head and adjusts the fit with an adjustable ratchet headgear (50)

by tightening knobs (60) and (70). The face shield (80) is attached to the ratchet headgear (50) by the side tightening knob (70) and is positioned in front of the user's face. The ultraviolet light source (10) is located over the face shield (80) and has a housing (20) for the ultraviolet LEDs (30). The ultraviolet light source (10) is positioned to emit ultraviolet light (dashed arrows) downward in front of and over the face shield (80). The ultraviolet reflector (85) is attached to the bottom of the face shield (80) and is configured to reflect ultraviolet light (dashed arrows) away from the user's torso to an area above or in front of the face shield (80).

Figure 5:
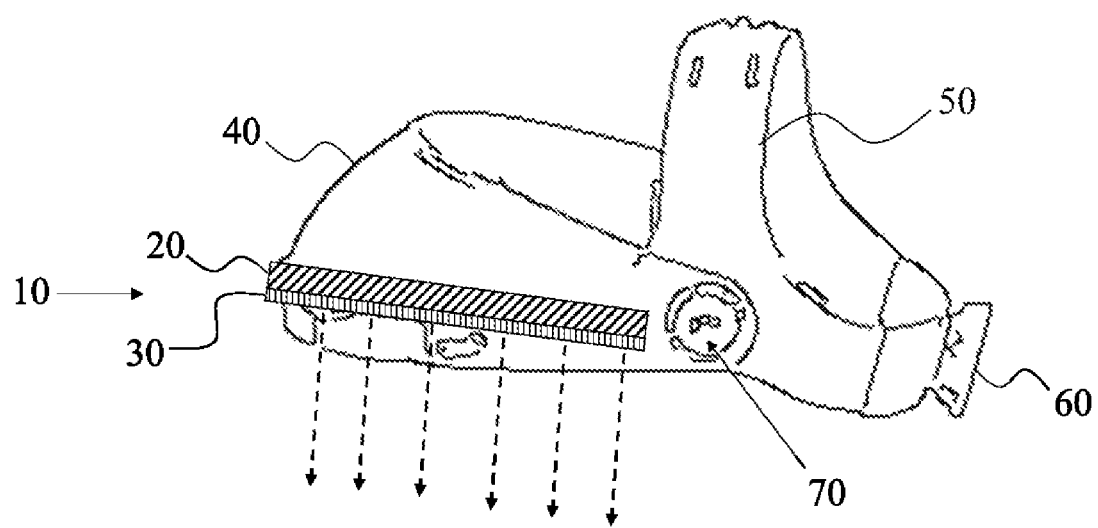
FIG. 5 is a perspective view of a ratchet headgear style head mount and ultraviolet light source.

In FIG. 5, the head mount (40) has an adjustable ratchet headgear (50) that can be configured to fit a user's head by tightening knobs (60) and (70). The ultraviolet light source (10) is attached to the head mount (40) and has a housing (20) for the ultraviolet LEDs (30). The ultraviolet light source (10) is positioned to emit ultraviolet light (dashed arrows) downward.

Figure 6:
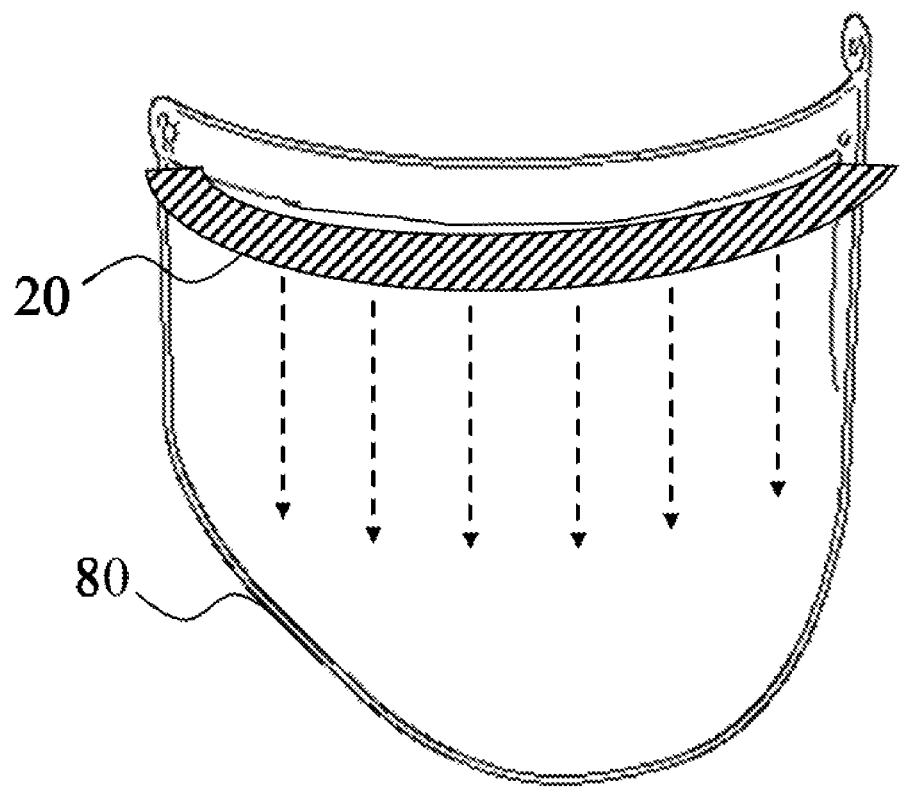
FIG. 6 is a perspective view of a face shield and ultraviolet light source.

In FIG. 6, the housing (20) is attached to the face shield (80) and is configured to direct ultraviolet light (dashed arrows) downward.

Figure 7:
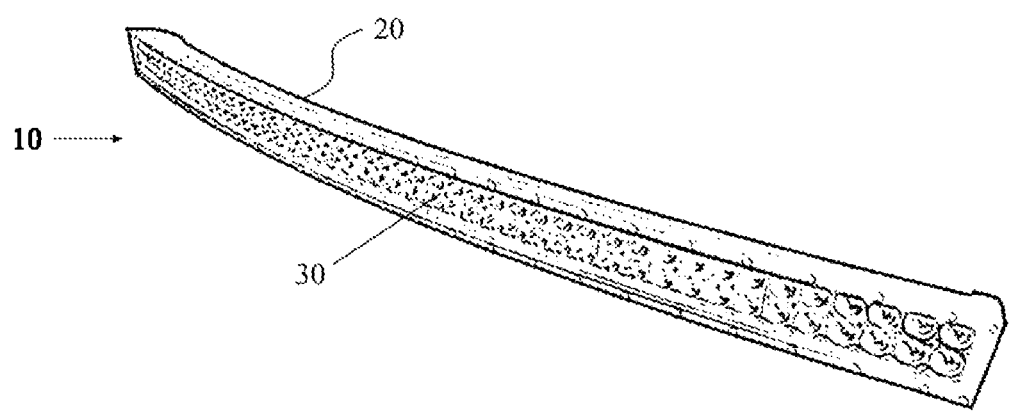
FIG. 7 is a perspective view of a curved ultraviolet light source.

In FIG. 7, the ultraviolet light source (10) has a housing (20) containing ultraviolet LEDs (30).

Figure 8:
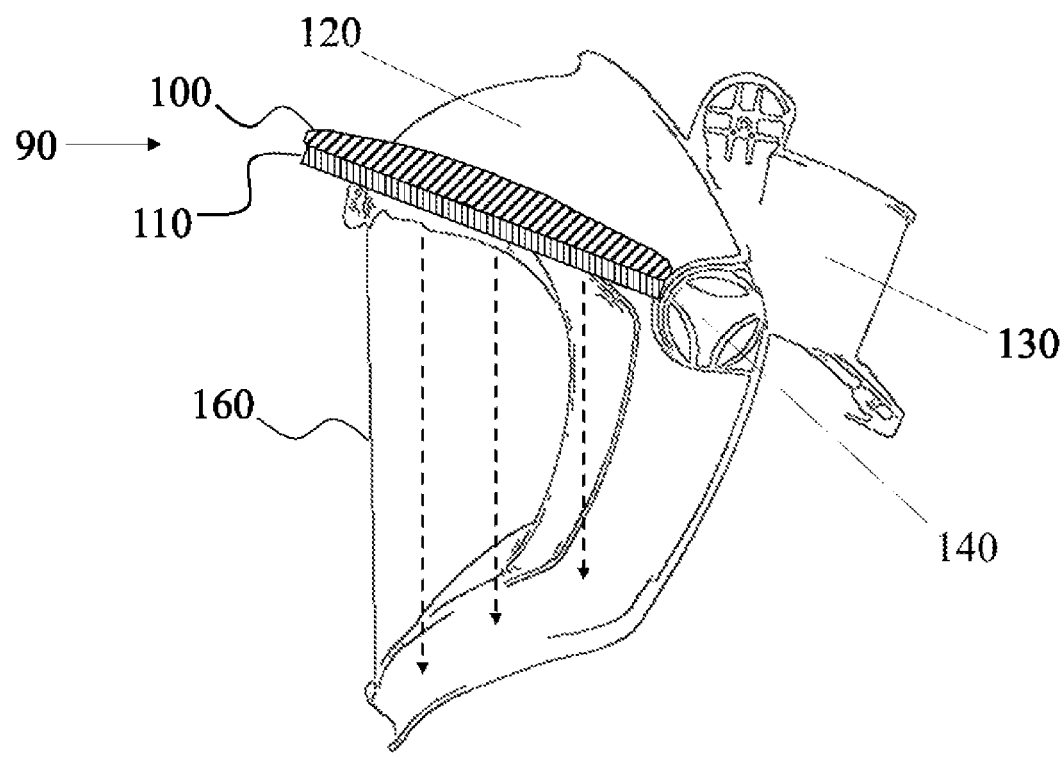
FIG. 8 is a perspective view of an ultraviolet face shield system including a full face helmet style head mount, face shield, and ultraviolet light source.

In FIG. 8, the full face head mount (120) has a wrap around headband (130) and can be configured to fit a user's head with a knob (140). The face shield (160) is attached to the head mount (120). The ultraviolet light source (90) is located over the face shield (160) and has a housing (100) for the ultraviolet LEDs (110). The ultraviolet light source (90) is positioned to emit ultraviolet light (dashed arrows) downward in front of and over the face shield (160).

Figure 9:
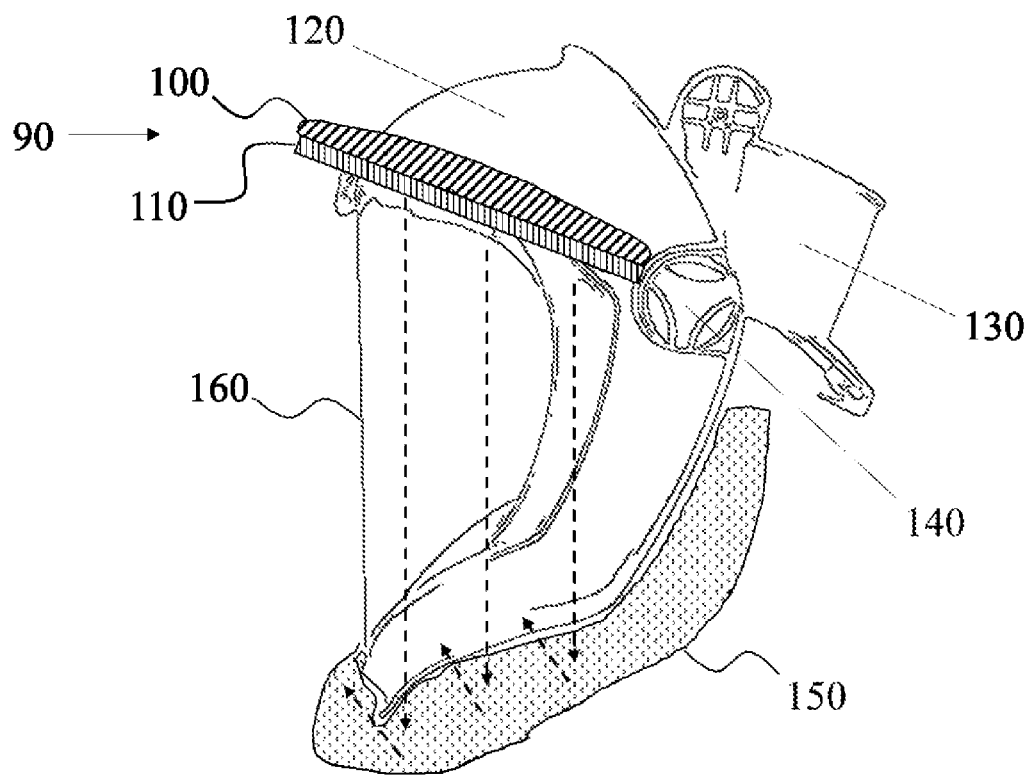
FIG. 9 is a perspective view of an ultraviolet face shield system including a full face helmet style head mount, face shield, ultraviolet light source, and ultraviolet reflector.

In FIG. 9, the full face head mount (120) has a wrap around headband (130) and can be configured to fit a user's head with a knob (140). The face shield (160) is attached to the full face head mount (120). The ultraviolet light source (90) is located over the face shield (160) and has a housing (100) for the ultraviolet LEDs (110). The ultraviolet light source (90) is positioned to emit ultraviolet light (dashed arrows) downward in front of and over the face shield (160). The ultraviolet reflector (150) is attached to the bottom of the full face head mount (120) and is configured to reflect ultraviolet light (dashed arrows).

Figure 10:
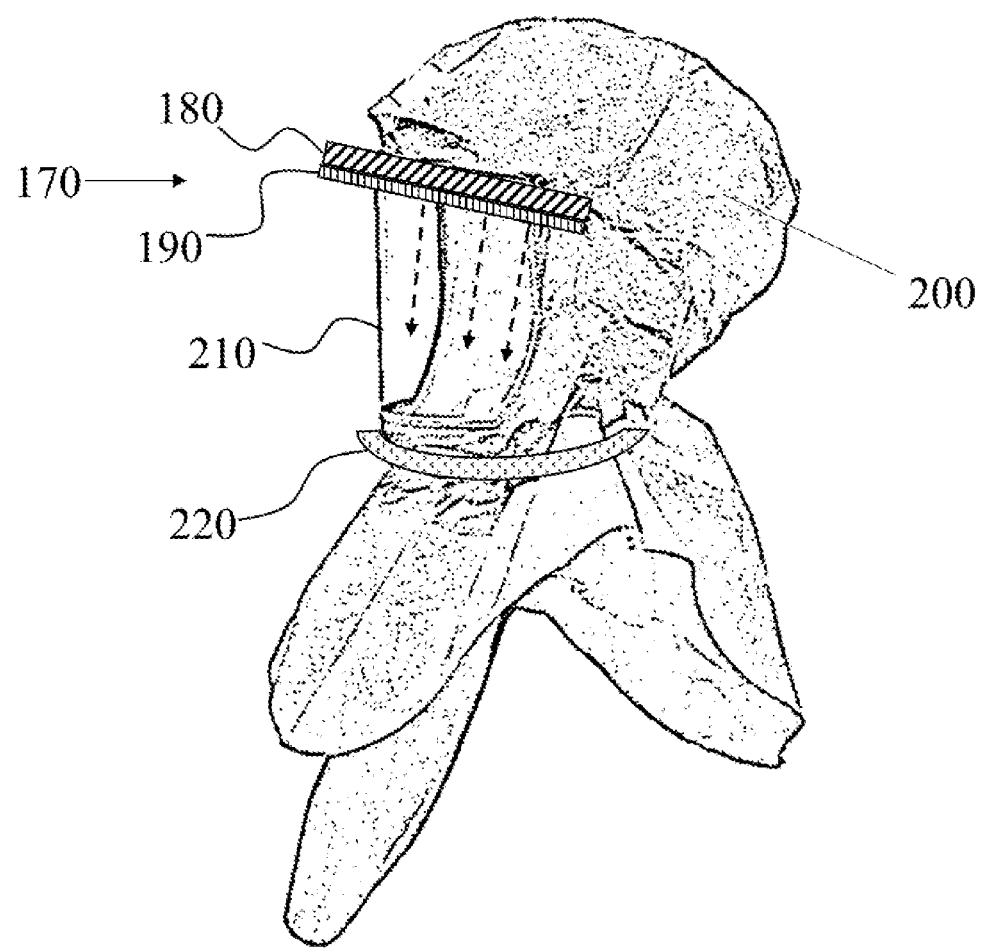
FIG. 10 is a perspective view of an ultraviolet face shield system including a hood style head mount, face shield, ultraviolet light source, and ultraviolet reflector.

In FIG. 10, the ultraviolet light source (170) has a housing (180) for the ultraviolet LEDs (190) and is attached to the hood head mount (200). The ultraviolet light source (170) is located over the face shield (210) and positioned to emit ultraviolet light (dashed arrows) downward in front of and over the face shield (210). The ultraviolet reflector (220) is located under the face shield (210) across from the ultraviolet light source (170) and is configured to reflect ultraviolet light (dashed arrows).

Figure 11:
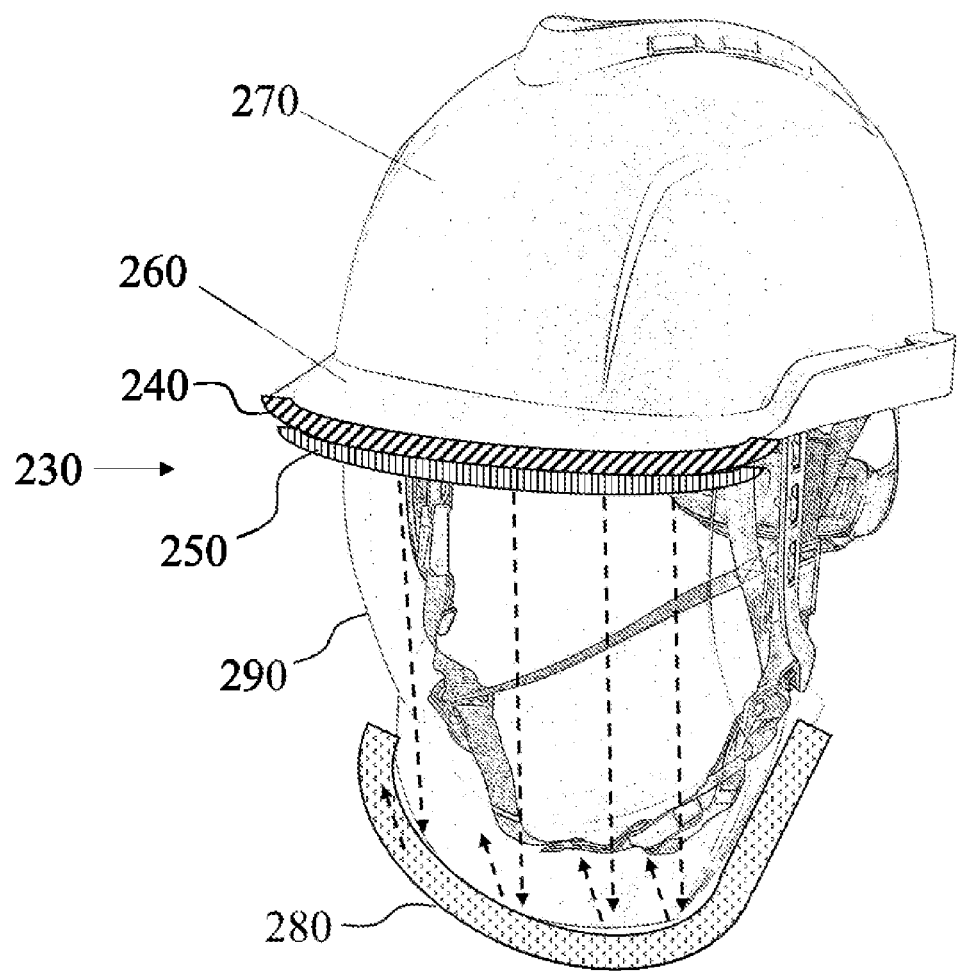
FIG. 11 is a perspective view of an ultraviolet face shield system including a hat style head mount, face shield, ultraviolet light source, and ultraviolet reflector.

In FIG. 11, the ultraviolet light source (230) has a housing (240) for the ultraviolet LEDs (250) and is attached to the hat head mount (270). The ultraviolet light source (230) is attached under the brim (260) of the hat head mount (270) and is located over the face shield (290) in a position to emit ultraviolet light (dashed arrows) downward in front of and over the face shield (290). The ultraviolet reflector (280) is located under the face shield (290) across from the ultraviolet light source (230) and is configured to reflect ultraviolet light (dashed arrows).

Figure 12:
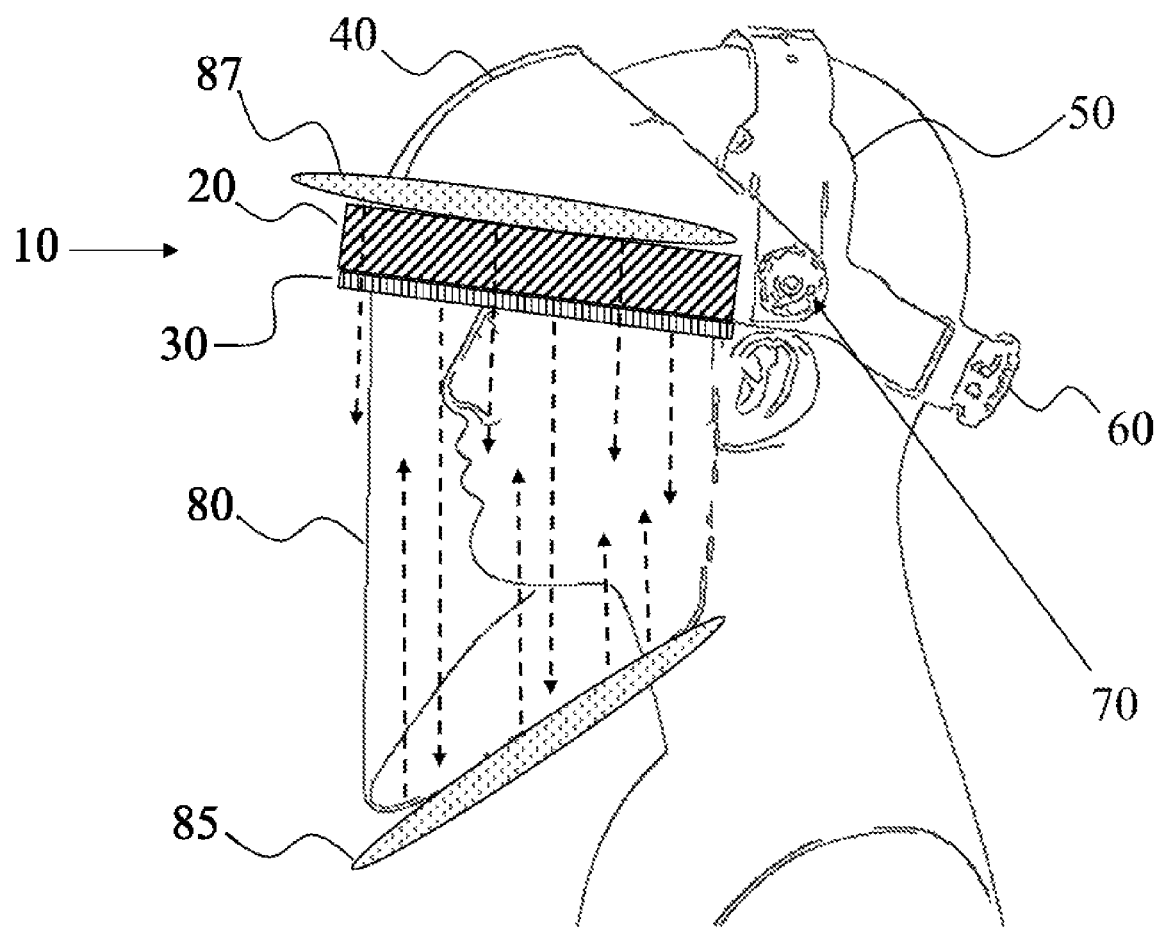
FIG. 12 is a perspective view of an ultraviolet face shield system including a ratchet headgear style head mount, face shield, ultraviolet light source, and two ultraviolet reflectors as worn by a user.

In FIG. 12, a user wears the head mount (40) over the head and adjusts the fit with an adjustable ratchet headgear (50) by tightening knobs (60) and (70). The face shield (80) is attached to the ratchet headgear (50) by the side tightening knob (70) and is positioned in front of the user's face. The ultraviolet light source (10) is located over the face shield (80) and has a housing (20) for the ultraviolet LEDs (30). The ultraviolet light source (10) is positioned to emit ultraviolet light (dashed arrows) downward in front of and over the face shield (80). The lower ultraviolet reflector (85) is attached to the bottom of the face shield (80) and is configured to reflect ultraviolet light (dashed arrows) away from the user's torso to an area above or in front of the face shield (80) and toward the upper ultraviolet reflector (87), which is positioned to reflect the ultraviolet light back down to the lower ultraviolet reflector (85) to repeat the cycle of reflection.

What is claimed:

1. An ultraviolet face shield system for reducing viral transmission comprising:
   a face shield comprising an inner surface configured for facing the face of a user and an outer surface;
   an adjustable head mount,
   at least one ultraviolet light source, and
   a first ultraviolet reflector attached to the face shield or head mount;
   wherein the ultraviolet light source is attached to the face shield or the head mount, positioned near the top of the face shield, and configured to emit ultraviolet light over the outer surface of the face shield; wherein the first ultraviolet reflector is positioned near the bottom of the face shield and protrudes outward from the face shield; wherein the first ultraviolet reflector comprises an upper surface and a lower surface wherein the upper surface of the first ultraviolet reflector faces the ultraviolet light source and is configured to reflect ultraviolet light emitted from the ultraviolet light source back towards the ultraviolet light source or away from the face shield; and wherein the ultraviolet light is capable of inactivating a virus.

2. The ultraviolet face shield system of claim 1, wherein the ultraviolet light source comprises an ultraviolet lamp or ultraviolet light emitting diode (LED) capable of emitting broad spectrum ultraviolet C (UVC) light having a wavelength between 200-400 nm or far-UVC spectrum light having a wavelength between 207-222 nm.

3. The ultraviolet face shield system of claim 2, wherein the face shield is curved, plastic, 8 to 15 inches wide, and 8 to 15 inches long, wherein the concave side of the curved plastic face shield is the inner surface of the face shield and the convex side of the curved plastic face shield is the outer surface of the face shield.

4. The ultraviolet face shield system of claim 3, wherein the head mount is a helmet, hood, hat, or ratchet headgear, and the face shield is attached to the head mount.

5. The ultraviolet face shield system of claim 1, wherein the ultraviolet face shield system comprises a second ultraviolet reflector attached to the face shield or head mount near the top of the face shield and protrudes from the face shield, wherein the ultraviolet light source is positioned between the first ultraviolet reflector and the second ultraviolet reflector, and wherein the second ultraviolet reflector comprises an upper surface and a lower surface wherein the lower surface of the second ultraviolet reflector faces the upper surface of the first ultraviolet reflector.

6. The ultraviolet face shield system of claim 5, wherein the first ultraviolet reflector comprises metal, aluminum, steel, silica, polytetrafluoroethylene (PTFE), mylar, or teflon.

7. The ultraviolet face shield system of claim 6, wherein the second ultraviolet reflector comprises metal, aluminum, steel, silica, polytetrafluoroethylene (PTFE), mylar, or teflon.

8. The ultraviolet face shield system of claim 7, wherein the face shield is polycarbonate, propionate, polyethylene, or acrylic.

9. The ultraviolet face shield system of claim 8, wherein the first ultraviolet reflector is elliptical, curved, circular, semicircular, or flat.

10. The ultraviolet face shield system of claim 9, wherein the second ultraviolet reflector is elliptical, curved, circular, semicircular, or flat.

11. The ultraviolet face shield system of claim 10, wherein the face shield is polycarbonate and the first and the second ultraviolet reflectors are aluminum.

12. The ultraviolet face shield system of claim 11, wherein the ultraviolet face shield system comprises a housing containing the ultraviolet light source, wherein the housing is swivelable and configured to adjust the direction the ultraviolet light source faces.

13. The ultraviolet face shield system of claim 12, wherein the head mount is a ratchet headgear.

14. The ultraviolet face shield system of claim 13, wherein the head mount is a hat comprising a brim and the ultraviolet light source is attached under the brim.

15. The ultraviolet face shield system of claim 11, wherein the ultraviolet face shield system further comprises goggles, glasses, a surgical mask, a N95 mask, or a N99 mask, wherein the goggles, glasses, surgical mask, N95 mask, N99 mask are positioned inside the ultraviolet face shield system.

16. The ultraviolet face shield system of claim 1, wherein the virus is COVID-19 virus.

17. The ultraviolet face shield system of claim 5, wherein the virus is COVID-19 virus.

18. A method of reducing viral transmission comprising wearing the ultraviolet face shield system of claim 1 and turning on the ultraviolet light source, thereby killing the virus.

19. The method of claim 18, wherein the virus is COVID-19 virus.

* * * * *